United States Patent
Simons et al.

(10) Patent No.: US 7,939,499 B2
(45) Date of Patent: May 10, 2011

(54) METHOD FOR INCREASING CARDIAC MASS AND PERFORMANCE

(75) Inventors: Michael Simons, Hanover, NH (US);
Daniella Tirziu, Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 737 days.

(21) Appl. No.: 11/913,097

(22) PCT Filed: May 2, 2006

(86) PCT No.: PCT/US2006/016621
§ 371 (c)(1),
(2), (4) Date: Oct. 30, 2007

(87) PCT Pub. No.: WO2006/119183
PCT Pub. Date: Nov. 9, 2006

(65) Prior Publication Data
US 2010/0256063 A1  Oct. 7, 2010

Related U.S. Application Data

(60) Provisional application No. 60/677,231, filed on May 3, 2005.

(51) Int. Cl.
*A61K 38/08* (2006.01)

(52) U.S. Cl. ...................... 514/16.4; 514/21.6
(58) Field of Classification Search .................. None
See application file for complete search history.

(56) References Cited

U.S. PATENT DOCUMENTS
2009/0226519 A1* 9/2009 Claude et al. ................. 424/484

FOREIGN PATENT DOCUMENTS
WO  0057895  10/2000
WO  0147540  7/2001

OTHER PUBLICATIONS

Harada et al. Basic Fibroblast Growth Factor Improves Myocardial Function in Chronically Ischemic Porcine Hearts. Journal of Clinical Investigation. Aug. 1994, vol. 94, pp. 623-630.*
Li et al. PR39, a peptide regulator of angiogenesis. Jan. 2000, Nature Medicine. vol. 6, No. 1, pp. 49-55.*
Bao et al., "PR-39 and PR-11 peptides inhibit ischemia-reperfusion injury by blocking proteasome-mediated I kappa B alpha degradation", Am J Physiol Heart Circ Physiol 2001 281:H2612-H2618.

* cited by examiner

*Primary Examiner* — Jeffrey E Russel
(74) *Attorney, Agent, or Firm* — Licata & Tyrrell P.C.

(57) ABSTRACT

The present invention relates to methods of using a proline/arginine-rich peptide such as PR11 or PR39 for increasing cardiac mass or performance and in the treatment of heart failure.

2 Claims, 1 Drawing Sheet

METHOD FOR INCREASING CARDIAC MASS AND PERFORMANCE

This application claims benefit of U.S. Provisional Patent Application Ser. No. 60/677,231, filed May 3, 2005, the content of which is incorporated herein by reference in its entirety.

This invention was made in the course of research sponsored by the National Institutes of Health (NIH Grant No. HL70247). The U.S. government may have certain rights in this invention.

BACKGROUND OF THE INVENTION

Congestive heart failure is a chronic, degenerative condition that impairs the heart's ability to pump blood at normal filling pressures to adequately meet the energy requirements of the body. It is estimated that 4.9 million Americans suffer from various degrees of congestive heart failure (CHF), with about 400,000 new cases identified each year. Heart failure is the most common diagnosis in hospital patients over the age of 65, and it carries a mortality rate higher than that for malignant tumors. One in five CHF patients dies within one year of diagnosis and only 15% survive more than 10 years.

There is no cure for CHF, short of a heart transplant. However, advances in pharmacology have provided improved treatment programs. Multidrug treatment regimens that include diuretics, vasodilators and inotropic agents such as angiotensin-converting enzyme (ACE) inhibitors, can slow the progression of CHF and reduce the number of acute episodes. However, treatment remains directed at symptoms and is most effective in the early stages of CHF.

In later stages of the disease, mechanical devices can play an important role. Left ventricular pacemakers can improve the heart's function as a pump, while cardiac assist devices may be used to help support the failing heart. These devices primarily address the needs of approximately 25% of CHF patients. Thus, there remains a need for improved treatments for patients with heart failure. The present invention meets this long-felt need.

SUMMARY OF THE INVENTION

The present invention is a method for increasing cardiac mass or performance in a subject. The method involves administering to a subject an effective amount of an agent which increases levels of a proline/arginine-rich peptide comprising SEQ ID NO:4 in the heart of the subject thereby increasing cardiac mass or cardiac performance in the subject.

The present invention is also a method for treating heart failure in a subject. This method involves administering to a subject, having or at risk of having heart failure, an effective amount of an agent which increases levels of a proline/arginine-rich peptide comprising SEQ ID NO:4 in the heart of the subject thereby treating heart failure in the subject.

DETAILED DESCRIPTION OF THE INVENTION

Figure 1:
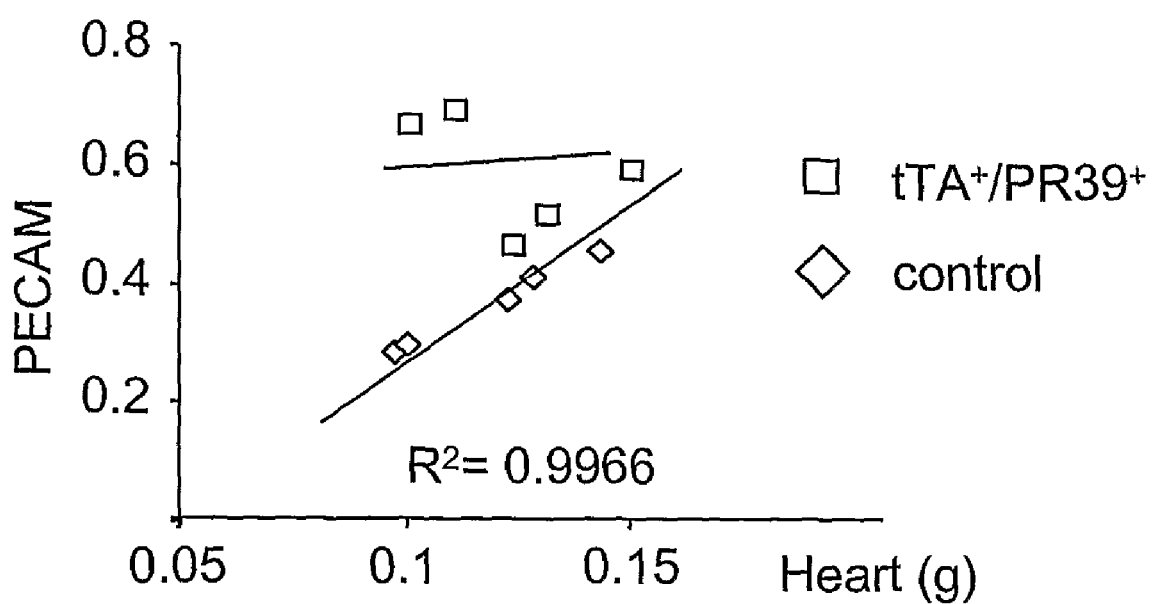
FIG. 1 depicts the correlation that exists between capillary density and myocardial mass in control animals and transgenic animals expressing PR39.

In case of the heart, excess physical load can induce cardiac enlargement and/or myocardial hypertrophy that represent an adaptive response to changing hemodynamic conditions. It has now been found that an increase in the endothelial cell mass in the normal heart in the absence of hemodynamic load can induce myocyte hypertrophy and result in a bigger, more efficiently functioning heart. The increase in the endothelial mass precedes the onset of myocardial enlargement by several weeks and the process stops when the capillary density per unit gram of myocardial tissue has returned to the baseline level. This endothelium-driven myocardial hypertrophy was achieved by cardiac-specific overexpression of an angiogenic proline/arginine-rich peptide, specifically PR39. PR39 was found to increase myocardial mass by 50% and cause a marked increase in both systolic and diastolic performance as well as ejection fraction and cardiac output of the heart. Accordingly, agents which increase cardiac levels of PR39 are useful in enhancing cardiac mass or performance and in the treatment of heart disease or disorders such as congestive heart failure and cardiomyopathies.

To demonstrate the efficacy of PR39, transgenic mice were generated with myocardial-specific expression of PR39 under control of a tetracycline-sensitive promoter. To monitor PR39 expression, β-galactosidase was expressed bicistronically. The withdrawal of tetracycline in these transgenic mice led to a marked increase in β-galactosidase expression that was comparable to that achieved by CMV promoter-driven expression and was completely suppressible by re-introduction of tetracycline. PCR analysis similarly confirmed that PR39 mRNA expression was induced by tetracycline withdrawal and was repressed by its re-introduction, while X-gal staining of the entire heart demonstrated inducible homogenous transgene expression.

Three weeks after induction of PR39 expression in 6-8 week-old mice, a significant increase in the endothelial cell mass was observed as determined by in vivo perfusion with an $I^{131}$-labeled anti-PECAM antibody and direct capillary counting (Table 1).

TABLE 1

| Mouse | Anti-PECAM (μg antibody/gram tissue) | Capillary Density (Capillary/50 μm$^2$) |
|---|---|---|
| Control | 0.31 ± 0.05* | 4.26 ± 0.10** |
| PR39 | 0.52 ± 0.07 | 5.90 ± 0.12 |

*p = 0.03,
**p < $10^{-21}$

Capillary density, which demonstrated very tight correlation with the myocardial mass in control animals, was much higher in the PR39 transgenics and increased out of proportion to the increase in the heart weight (FIG. 1).

Six weeks after induction of PR39 expression, a large increase in the heart size was observed that was attributable to increased ventricular wall thickness and a mild increase in the left ventricle chamber size. Heart size significantly increased from 0.115±0.01 gram in non-transgenic mice to 0.15±0.01 gram in transgenic mice expressing PR39 and remained unchanged after 3 weeks repression of PR39 expression. Examination of enzymatically dispersed cardiac myocytes showed a marked increase in their cross-sectional area that was proportional to the overall increase in heart size (35% heart enlargement vs. 30% myocyte area increase).

Quantification of endothelial cell mass and capillary density showed that while it was unchanged from week 3, the capillary density per gram of myocardial tissue in transgenic mice returned to values seen in control mice. Immunocytochemical staining with anti-Ki67 antibody demonstrated increased proliferation of endothelial cells between myocyte bundles, but no proliferation of cardiac myocytes themselves was noted in multiple sections. To gain further insight into the nature of the hypertrophy process, expression of myocyte hypertrophy markers was examined. There was a marked increase in ANF, βMHC and skeletal α-actin gene expression 6 weeks, but not 3 weeks, after PR39 expression induction. These findings are consistent with an increase in endothelial cell mass, preceded by an increase in cardiac size, largely driven by myocyte hypertrophy accompanied by an induction of a typical hypertrophic response.

To determine whether this endothelial-driven myocardial hypertrophy affected cardiac performance, echocardiographic and pressure-volume loop analysis of myocardial function was performed following induction of PR39 expression. In agreement with morphologic observations, heart expressing PR39 had somewhat larger left ventricular end-diastolic volume and end-diastolic diameter (Table 2). There was a significant enhancement of systolic performance as indicated by decreased left ventricle end-systolic volume and increases in the injection fraction, +dP/dT, maximal-generated left ventricle pressure and cardiac output (Table 2). Unexpectedly, there was also a significant improvement in diastolic function as indicated by reduced tau and −dP/dt (Table 2).

TABLE 2

| Parameter | Control | PR39 |
| --- | --- | --- |
| Left Ventricle Mass (mg)* | 67 ± 0.4 | 74 ± 1.1$^a$ |
| Maximum volume (μL) | 17.45 ± 0.14 | 20.15 ± 0.29$^a$ |
| Minimum volume (μL) | 5.92 ± 0.25 | 2.86 ± 0.13$^a$ |
| End systolic volume (μL) | 7.34 ± 0.34 | 3.26 ± 0.15$^a$ |
| End diastolic volume (μL) | 16.17 ± 0.16 | 18.78 ± 0.31$^a$ |
| Maximum pressure (mmHg) | 78.47 ± 1.58 | 92.26 ± 0.54$^a$ |
| Minimum pressure (mmHg) | 2.39 ± 0.11 | 3.79 ± 0.15$^a$ |
| End systolic pressure (mmHg) | 68.61 ± 1.26 | 70.49 ± 0.99$^b$ |
| End diastolic pressure (mmHg) | 4.71 ± 0.14 | 7.17 ± 0.17$^a$ |
| Left Ventricle internal dimension systolic (mm)* | 1.36 ± 0.1 | 2.28 ± 0.20$^c$ |
| Maximum dP/dt (mmHg/second) | 6033 ± 213 | 8809 ± 167$^a$ |
| Minimum dP/dt (mmHg/second) | −5129 ± 174 | −7503 ± 123$^a$ |
| Tau-w (msec) | 7.79 ± 0.18 | 6.0 ± 0.1$^a$ |
| Stroke volume (μL) | 11.53 ± 0.27 | 17.29 ± 0.32$^a$ |
| Ejection fraction (%) | 66.07 ± 1.44 | 85.06 ± 0.76$^a$ |
| Cardiac output (μL/minute) | 5592 ± 180 | 9046 ± 239$^a$ |

$^a$P < 0.0001,
$^b$P = 0.078.
$^c$p < 0.001
*Parameter was determined six weeks following induction of PR39 expression. All other parameters were determined six weeks following induction of PR39 expression followed by 3 weeks repression of PR39 expression.

To evaluate the robustness of the observed increase in myocardial size and functional improvement, PR39 expression was shut off six weeks after its induction and the mice were re-examined three weeks later. Both the increase in the myocardial mass and improvements in the systolic and diastolic function were maintained at that time.

These results demonstrate that an increase in the organ endothelial cell mass can drive a size increase that, in the case of myocardium, results in improved functional performance. This increase stopped when the capillary density per gram of tissue returned to control levels, indicating that this may be a crucial parameter regulating cardiac size. The increase in size was largely mediated by an increase in myocyte diameter and not by myocyte proliferation. The molecular signature of the observed hypertrophic response appeared very similar to that of pressure-induced hypertrophy. However, while systolic function is improved in both cases, typically diastolic function is reduced in the case of pressure-induced hypertrophy and improved in the case of endothelial-driven hypertrophy. It is contemplated that this is the result of myocardial oxygen demand mismatch in cases of severe pressure overload due to the insufficient arterial supply of hypertrophied myocardium.

In light of the novel findings disclosed herein, the present invention is a method for increasing or enhancing cardiac mass or performance in a subject by administering to the subject an effective amount of an agent which results in increased levels of a proline/arginine-rich (PR) peptide in the heart of the subject thereby increasing cardiac mass or cardiac performance. In one embodiment of the instant method, the agent increases both cardiac mass and cardiac performance. In another embodiment, mass of the left ventricle is increased.

As used herein, cardiac performance is defined by various parameters including, but not limited to, end diastolic volume (i.e., the volume of blood in each ventricle at the end of diastole, usually about 120-130 mL in the normal human heart; it is a measure of preload and is the sum of the stroke volume plus end systolic volume), end systolic volume (i.e., the volume of blood remaining in each ventricle at the end of systole, usually about 50-60 mL in the normal human heart; it is the difference between the end diastolic volume and the stroke volume and is determined by the contractility of the ventricles and the state of the venous system), ejection fraction (i.e., the percentage of blood volume held within the left ventricle at the end of diastole which is ejected into the vasculature as the stroke volume), cardiac output (i.e. the product of heart rate and stroke volume), maximum blood pressure (i.e., systolic blood pressure occurring near the end of the stroke output of the left ventricle of the heart, usually about 120 millimeters of Mercury in the normal human heart) and minimum blood pressure (i.e., diastolic blood pressure occurring late in ventricular diastole, usually about 70 millimeters of Mercury in the normal human heart).

In general, a subject in need of such treatment is one in need of increased blood flow or increased cardiac output, e.g., a subject with a disease or condition which results in decreased blood flow or decreased cardiac output. By administering to the subject an effective amount of an agent which increases levels of PR peptide in the heart, cardiac mass or at least one of the parameters associated with cardiac performance is increased. In particular embodiments, the agent increases cardiac mass or a cardiac performance parameter by about 10%, 20%, 25%, 30%, 35%, 40%, 45%, 50%, 60%, 70%, 80% or more as compared to cardiac mass or a performance parameter in the absence of the agent.

Increasing or enhancing cardiac performance is useful as a research tool for studying cardiac function and for preventing or treating cardiac diseases or conditions which are associated with decreased cardiac output (e.g., congestive heart failure).

Therefore, the present invention is also a method for treating heart failure in a subject having or at risk of having heart failure by administering to the subject an effective amount of an agent which increases levels of a PR peptide in the heart, thereby treating heart failure in the subject. As used herein, heart failure refers to an abnormality of cardiac function where the heart does not pump blood at the rate needed for the requirements of metabolizing tissues. Heart failure can be the result of cardiac diseases including, but not limited to, congestive heart failure, myocarditis, congestive cardiomyopathy, restrictive cardiomyopathy, and cardiac tumors, inherited genes or traits that dispose or predispose to altered contractile function, alone or in combination with other injury or stimuli, along with any cardiovascular disease or disorder associated with decreased cardiac output.

The terms treat or treatment refer to both therapeutic treatment and prophylactic or preventative measures, wherein the object is to prevent or slow down (lessen) an undesired physiological change or disorder, such as the development of congestive heart failure, cardiomyopathy, etc. For purposes of this invention, administration of an effective amount of an agent disclosed herein results in a beneficial or desired clinical result including, but are not limited to, alleviation of symptoms (e.g., fatigue, malaise or chest pain), diminishment of extent of disease, stabilized (i.e., not worsening) state of disease, delay or slowing of disease progression, amelioration or palliation of the disease state, and remission (whether partial or total), whether detectable or undetectable. Treatment can also mean prolonging survival as compared to expected survival if not receiving treatment. Those in need of treatment include those already with the condition or disorder as well as those at risk of having the condition or disorder (e.g., subjects disposed or predisposed to altered cardiac function based on genetics or life-style). In one embodiment, treatment is provided to a subject exhibiting signs or symptoms of heart failure. In another embodiment, treatment is provided to a subject at risk of heart failure as a preventive measure.

In the context of the methods of the present invention, a subject is intended to include any animal classified as a mammal, including humans, domestic and farm animals, as well as zoo, sport, or companion animals, such as dogs, horses, cats, cows, etc. which would benefit from increased or enhanced cardiac performance or prevention or treatment of heart failure.

As used in the context of the present invention, an agent which increases levels of a PR peptide in the heart is intended to include a PR peptide itself (e.g., a PR39 prepropeptide, a PR39 propeptide, or a mature PR39 peptide), a biologically active fragment of PR39 peptide (e.g., PR11), or a PR39 or PR11 peptide variant which retains the biological activity of PR39 and PR11. An agent which increases levels of a PR peptide in the heart is also intended to include a nucleic acid encoding a PR39 peptide, a biologically active fragment of PR39 peptide, or a PR39 peptide variant.

A mature PR39 peptide is derived from a prepropeptide. By way of illustration, a porcine PR39 prepropeptide is set forth herein as SEQ ID NO:1. Referring to SEQ ID NO:1, amino acid residues 1 to 29 encompass the signal sequence of the prepropeptide and amino acid residues 30 to 130 represent propeptide sequences. The mature PR39 peptide ends with a proline amide with glycine-170 providing the amide group and, thus C-terminal resides 170 to 172 are absent in the mature peptide. Exemplary propeptide PR39 and mature PR39 peptide sequences are set forth herein as SEQ ID NO:2 and SEQ ID NO:3, respectively. PR11 is a C-terminal truncated form of PR39 with 11 N-terminal amino acids remaining. As PR11 has been demonstrated in the art to retain the biological functions of mature PR39 protein (see, e.g., Bao, et al. (2001) *Am. J. Physiol. Heart Circ. Physiol.* 281:H2612-H2618), particular embodiments of the present invention embrace the use of a PR peptide having at least the 11 N-terminal amino acid residues of PR39 set forth in SEQ ID NO:4. In other embodiments, a PR peptide comprises at least the amino acid residues of PR39, i.e., SEQ ID NO:3.

A nucleic acid encoding a PR peptide of the present invention includes nucleic acids encoding a PR peptide or biologically active peptide fragments or variants thereof. An exemplary nucleic acid encoding a PR39 prepropeptide, and accordingly a PR39 propeptide, a mature PR39 peptide and a PR11 peptide, is set forth herein as SEQ ID NO:5. A nucleic acid that is substantially similar to a nucleic acid encoding a PR peptide is also encompassed within the context of a nucleic acid encoding a PR peptide. A nucleic acid that is substantially similar to a nucleic acid encoding a PR peptide shares at least 70% identity over its entire length with a nucleic acid sequence encoding a PR peptide peptide of SEQ ID NO:1, SEQ ID NO:2, SEQ ID NO:3 or SEQ ID NO:4, and a nucleic acid having a nucleic acid sequence that is at least 70% identical to that of SEQ ID NO:5, over its entire length. In particular embodiments, a nucleic acid that is substantially similar to a nucleic acid encoding a PR peptide shares at least 80% identity, at least 90% identity, at least 95% identity, or more desirably at least 97-99% identity, to that of a nucleic acid encoding a PR peptide of SEQ ID NO:1, SEQ ID NO:2, SEQ ID NO:3 or SEQ ID NO:4 over the entire length of such a nucleic acid.

In accordance with the present invention, nucleic acids having the appropriate level sequence homology (i.e., 70% identity or greater) with part or all the coding regions of a nucleic acid encoding a PR peptide can be identified by using hybridization and washing conditions of appropriate stringency. For example, hybridizations can be performed, according to the method of Sambrook, et al. ((1989) *Molecular Cloning, a Laboratory Manual*, Cold Spring Harbor Laboratories, New York) using a hybridization solution containing 1.0% SDS, up to 50% formamide, 5×SSC (150 mM NaCl, 15 mM trisodium citrate), 0.05% sodium pyrophosphate (pH 7.6), 5×Denhardt's solution, and 100 microgram/mL denatured, sheared salmon sperm DNA. Hybridization is carried out at 37-42° C. for at least six hours. Following hybridization, filters are washed as follows: 5 minutes at room temperature in 2×SSC and 1% SDS; 15 minutes at room temperature in 2×SSC and 0.1% SDS; 30 minutes to 1 hour at 37° C. in 2×SSC and 0.1% SDS; and 2 hours at 45-55° C. in 2×SSC and 0.1% SDS, changing the solution every 30 minutes.

Oligonucleotides having sequences capable of hybridizing with at least one sequence of a nucleic acid molecule encoding a PR peptide can also be used as probes for the detection and isolation of nucleic acids encoding a PR peptide from cDNA libraries from, e.g., human, bovine, canine, and feline to obtain PR peptide homologs from human, bovine, canine, and feline, respectively.

When the nucleic acids of the invention are used for production of a PR peptide in vitro, in vivo or ex vivo, the nucleic acid can include the coding sequence for the mature PR39 peptide or a fragment thereof, by itself; or the coding sequence for the mature PR39 peptide or fragment in reading frame with other coding sequences, such as those encoding a leader or secretory sequence, a pre-, or pro- or prepropeptide sequence, or other fusion protein. For example, a marker sequence which facilitates purification of a fused PR peptide can be encoded by an in vitro expression vector. The nucleic acid encoding a PR peptide can also contain non-coding 5' and 3' sequences, such as transcribed, non-translated sequences, splicing and polyadenylation signals, ribosome binding sites and sequences that stabilize mRNA. Such sequences are well-known to the skilled artisan and can be obtained from the PR39 locus or from another unrelated gene.

Nucleic acids of the present invention can be maintained in vitro as DNA in any convenient cloning vector, e.g., in plasmid cloning/expression vector, to produce large quantities of a substantially pure PR peptide, or fragments thereof. An expression vector harboring a nucleic acid encoding a PR peptide generally contain all the necessary regulatory sequences, for example, promoter and terminator sequences, operably linked to the nucleic acid encoding a PR peptide such that the PR peptide coding sequence is transcribed into RNA and subsequently translated into protein. Large numbers of suitable vectors and regulatory sequences are known to those of skill in the art, and are commercially available. The following vectors are provided by way of example, bacterial vectors pQE70, pQE60, pQE-9 (QIAGEN®), pBS, pD10, pBLUESCRIPT® SK, pBSKS, pNH8A, pNHI8A, pNH46A (STRATAGENE®) and pRIT5 (Pharmacia); and eukaryotic vectors pWLNEO, pSV2CAT, pOG44, PXTI, pSG (STRATAGENE®) pSVK3, pBPV, pMSG, PSVL (Pharmacia). As further examples, a PR peptide cDNA can be inserted in the pEF/myc/cyto vector (INVITROGEN™) or the pCMV-Tag3b vector (STRATAGENE®) and transformed (e.g., calcium phosphate transfection, DEAE-dextran-mediated transfection, microinjection, cationic lipid-mediated transfection, electroporation) into HeLa thereby facilitating purification and use of a PR peptide.

However, any other plasmid or vector can be used as long as they are replicable and viable in the host. In addition, a complete mammalian transcription unit and a selectable marker can be inserted into a prokaryotic plasmid for use in in vivo procedures. The resulting vector is then amplified in bacteria before being transfected into cultured mammalian cells or delivered directly to a subject with an acceptable carrier. Examples of vectors of this type include pTK2, pHyg and pRSVneo. Hence, these plasmids, constructs and vectors can be used in both in vitro and in vivo procedures.

Representative examples of appropriate hosts for in vitro procedures include bacterial cells, such as streptococci, staphylococci, *E. coli, Streptomyces* and *Bacillus subtilis* cells; fungal cells, such as yeast cells and *Aspergillus* cells, insect cells such as *Drosophila* S2 and *Spodoptera* Sf9 cells; animal cells such as CHO, COS, HeLa, C127, 3T3, BHK, and HEK 293 cells, and plant cells. When the nucleic acid encoding a PR peptide encodes a PR39 prepropeptide or propeptide, it can be particularly advantageous that a neutrophil, bone marrow, endothelial cell, or small intestine cell or cell line be used for recombinant peptide production for proper processing and secretion of a mature PR39 peptide (Shi, et al. (1994) *J. Leukoc. Biol.* 56(6):807-11; Li, et al. (2000) *Nat. Med.* 5:49-55; Storici and Zanetti (1993) *Biochem. Biophys. Res. Commun.* 196 (3):1058-1065). The selection of an appropriate host is deemed to be within the scope of those skilled in the art from the teachings herein.

An expression vector harboring a nucleic acid encoding a PR peptide can also be used for in vivo or ex vivo therapeutic expression (i.e., gene therapy). Such a gene transfer vector includes, but is not limited to, a naked plasmid, a viral vector, such as an adenovirus, an adeno-associated virus, a herpes-simplex virus based vector, a lentivirus vector such as those based on the human immunodeficiency virus (HIV), a vaccinia virus vector, a synthetic vector for gene therapy, and the like (see Miller and Rosman (1992) *BioTechniques* 7:980-990; Anderson, et al. (1998) *Nature* 392:25-30; Verma and Somia (1997) *Nature* 389:239-242; Wilson (1996) *New Engl. J. Med.* 334:1185-1187; Suhr, et al. (1993) *Arch. Neurol.* 50:1252-1268). For example, a gene transfer vector employed herein can be a retroviral vector. Retroviral vectors contemplated for use herein are gene transfer plasmids that have an expression construct, i.e., a nucleic acid encoding a PR peptide operatively linked to an appropriate promoter and terminator sequence, residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. Nos. 5,399,346 and 5,252,479; and in WO 92/07573, WO 90/06997, WO 89/05345, WO 92/05266 and WO 92/14829. These documents provide a description of methods for efficiently introducing nucleic acids into human cells using such retroviral vectors. Other retroviral vectors include, for example, mouse mammary tumor virus vectors (e.g., Shackleford, et al. (1988) *Proc. Natl. Acad. Sci. USA* 85:9655-9659), human immunodeficiency virus (e.g., Naldini, et al. (1996) *Science* 272:165-320), and the like.

Various procedures are also well-known in the art for providing helper cells that produce retroviral vector particles that are essentially free of replicating virus. See, for example, U.S. Pat. No. 4,650,764; Miller (1990) *Human Gene Therapy* 1:5-14; Markowitz, et al. (1988) *J. Virol.* 61(4):1120-1124; Watanabe, et al. (1983) *Mol. Cell. Biol.* 3(12):2241-2249; Danos, et al. (1988) *Proc. Natl. Acad. Sci. USA,* 85:6460-6464; and Bosselman, et al. (1987) *Mol. Cell. Biol.* 7(5): 1797-1806, which disclose procedures for producing viral vectors and helper cells that minimize the chances for producing a viral vector that includes a replicating virus.

An exemplary gene transfer vector is a replication-deficient adenovirus carrying a nucleic acid encoding a PR peptide to effect increases in cardiac mass or performance in a subject suffering from or at risk of heart failure. When used in combination with catheter-mediated infusion, such replication-defective adenovirus vectors have provided prolonged recombinant gene expression in the myocardium (Barr, et al. (1994) *Gene Ther.* 1(1):51-8; Ding, et al. (2004) *Gene Ther.* 11(3):260-5). In general, a nucleic acid encoding a PR peptide can be transferred into the heart, including cardiac myocytes, in vivo and direct constitutive production of a PR peptide.

For ex vivo applications, adult bone marrow cells can be obtained from the subject being treated and grown under suitable culture conditions in a container for a period of time sufficient to promote production by the bone marrow of early attaching cells. The early attaching cells are transfected in culture with a vector as described herein containing a nucleic acid encoding a PR peptide and the transfected early attaching cells (and/or medium in which they are cultured after transfection) are then directly administered (e.g., catheter-mediated infusion) to a desired site such as the myocardium in the subject so as to deliver to the site the expressed PR peptide. Advantageously, transfected cells for ex vivo therapy can secrete the PR peptide to effect non-transfected cells at the site of infusion.

Depending on the gene transfer vector selected and the mode of administration (i.e., catheter-mediated infusion, i.p. injection, or ex vivo cell delivery), a nucleic acid encoding a PR peptide can be operatively linked to a variety of promoters to control initiation of mRNA transcription. Such promoters typically contain at least a minimal promoter in combination with a regulatory element which mediates temporal and/or spatial expression. When constitutive high-level expression is desired and the gene transfer vector is to be infused directly into myocardial tissue, a constitutive promoter such as CMV immediate early, HSV thymidine kinase, early and late SV40 can be selected. When myocardial-specific expression is desired, a myocardial-specific promoter such as a α-myosin heavy chain promoter (Li, et al. (2000) supra; Kang, et al. (2005) *J. Nucl. Med.* 46(3):479-83) can be employed.

As an alternative to viral-mediated transduction of host cells, therapeutic nucleic acids can be delivered to target cells via basic transfection methods such as permeabilizing the cell membrane physically or chemically. Liposomes or protein conjugates formed with certain lipids and amphophilic peptides can also be used for transfection (Stewart, et al. (1992) *Hum. Gene Ther.* 3(3):267-75; Zhu, et al. (1993) *Science* 261(5118):209-11). Such an approach is desirable when naked DNA or plasmid vectors are employed for expressing a PR peptide.

In addition to therapeutic uses and recombinant protein production, vectors and host cells disclosed herein are useful for producing transgenic animals which overexpress a PR peptide.

As an alternative to in vivo or ex vivo expression methods of introducing a PR peptide in the subject being treated, a PR39 peptide itself, or variant or fragment thereof (e.g., PR11), can be administered to the subject to effect an increase in cardiac mass or performance and in the treatment of heart failure. In particular embodiments, the PR peptide administered encompasses at least the 11 N-terminal amino acid residues of PR39. Exemplary peptides are set forth herein in SEQ ID NOs:1-4. In particular embodiments of the present invention, when a purified PR39 peptide is administered, a mature PR39 peptide is selected. In general, a mature PR39 peptide has a sequence which is substantially similar to that of SEQ ID NO:3. The term substantially similar refers to PR39 variants (e.g., peptides with conservative substitutions and/or variations) that do not materially affect the nature of the peptide (i.e., the structure, stability characteristics, specificity and/or biological activity of the peptide for enhancing cardiac mass and performance). In general, a PR39 peptide having an amino acid sequence that is substantially similar to SEQ ID NO:3 shares at least 70% identity with that of SEQ ID NO:3, over its entire length and exhibits at least one biological activity of PR39. The present invention further provides for a PR39 peptide which has an amino acid sequence which shares at least 80% identity, at least 90% identity, at least 95% identity, or more desirably at least 97-99% identity, to that of SEQ ID NO:3 over the entire length of SEQ ID NO:3.

Percent identical and percent similar are used herein in comparisons among amino acid and nucleic acid sequences. When referring to amino acid sequences, identity or percent identical refers to the percent of the amino acids of the subject amino acid sequence that have been matched to identical amino acids in the compared amino acid sequence by a sequence analysis program. Percent similar refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are well-known in the art (see, e.g., Taylor (1986) *J. Theor. Biol. H* 9:205). When referring to nucleic acid molecules, percent identical refers to the percent of the nucleotides of the subject nucleic acid sequence that have been matched to identical nucleotides by a sequence analysis program.

Identity and similarity can be readily calculated by known methods. Nucleic acid sequences and amino acid sequences can be compared using computer programs that align the similar sequences of the nucleic or amino acids thus define the differences. Such methods include the BLAST programs (NCBI) and the DNAstar system (Madison, Wis.). However, equivalent alignments and similarity/identity assessments can be obtained through the use of any standard alignment software. For instance, the GCG Wisconsin Package, available from the Genetics Computer Group in Madison, Wis., can also be used to compare sequence identity and similarity.

In some embodiments, a PR peptide of the present invention embraces a PR11 peptide or a mature PR39 protein (i.e. lacking pre and pro sequences) as part of a larger protein, such as a fusion protein. It is often advantageous to include additional amino acid sequences which contain secretory sequences or sequences which aid in purification or stability of the PR peptide.

In addition to PR11, other fragments of a mature PR39 peptide are also included in the invention. For example, a PR39 peptide fragment is a peptide having an amino acid sequence that is entirely the same as part, but not all, of the amino acid sequence of the mature PR39 peptide and is desirably biologically active (i.e., the ability to increase cardiac mass or performance). Fragments include, for example, truncation peptides having the amino acid sequence of a mature PR39 peptide, except for deletion of a continuous series of residues that includes, e.g., the carboxyl terminus (see, e.g., Chan, et al. (2001) *J. Invest. Dermatol.* 116(2):230-5).

A PR peptide of the invention can be prepared in any suitable manner. If produced in situ, the peptide can be purified from appropriate sources, e.g., neutrophils, intestinal cells, spleen cells (Bonetto, et al. (1999) *Cell Mol. Life Sci.* 56:174-8).

Alternatively, the availability of nucleic acid molecules encoding the PR39 peptide enables production of PR peptides of the invention using cell-free translation methods known in the art. For example, a cDNA or gene can be cloned into an appropriate transcription vector for in vitro transcription, followed by cell-free translation in a suitable cell-free translation system. In vitro transcription and translation systems are commercially available, e.g., from PROMEGA® Biotech, Madison, Wis., or GIBCO-BRL®, Rockville, Md. In vitro transcription and translation is suitable for preparing small amounts of native or mutant proteins for research purposes.

Larger quantities of PR peptide can be produced by in vitro expression in a suitable prokaryotic or eukaryotic system as disclosed herein. Suitable vectors for recombinant protein expression in mammalian, yeast, or prokaryotic systems are commercially available from such sources as STRATAGENE®, INVITROGEN™, Pharmacia and the like.

Host-specific secretion signals can be used to facilitate purification of the resulting peptide. The coding sequence for the secretion peptide is operably linked to the 5' end of the coding sequence of the PR peptide, and this hybrid nucleic acid molecule is inserted into a plasmid adapted to express the peptide in the host cell of choice. Plasmids specifically designed to express and secrete foreign proteins are available from commercial sources. For example, if expression and secretion is desired in *E. coli*, commonly used plasmids include pTrcPPA (Pharmacia); pPROK-C and pKK233-2 (CLONTECH™); and pNH8a, pNH16a, pcDNAII and pAX (STRATAGENE®), among others.

An in situ purified PR peptide or a PR peptide produced by cell-free transcription/translation or by gene expression in a recombinant prokaryotic or eukaryotic system can be purified according to methods known in the art (e.g., fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; or gel filtration using, for example, SEPHADEX® G-75). Purified PR peptide can be further modified before therapeutic use. For example, purified PR39 peptide can be digested with carboxypeptidases P and Y (see, Bonetto, et al. (1999) supra) to produce a biologically active PR39 peptide.

Alternatively, a synthetic PR peptide can be prepared using various synthetic methods of peptide synthesis via condensation of one or more amino acid residues, in accordance with conventional peptide synthesis methods. For example, peptides are synthesized according to standard solid-phase methodologies, such as may be performed on an APPLIED BIO-SYSTEMS™ Model 430A peptide synthesizer (APPLIED BIOSYSTEMS™, Foster City, Calif.), according to manufacturer's instructions. Other methods of synthesizing peptides or peptidomimetics, either by solid phase methodologies or in liquid phase, are well-known to those skilled in the art.

Further, purified mature PR39 or PR11 peptide can be obtained from a commercial source such as *Phoenix* Pharmaceuticals, Inc. (Belmont, Calif.).

Independent of the source, a PR peptide of the present invention can be formulated into a pharmaceutically acceptable composition for therapeutic use in accordance with the methods disclosed herein. Advantageously, mature PR39 peptide rapidly enters cells (Chan, et al. (1998) supra) and therefore a PR peptide can be formulated with any suitable pharmaceutically acceptable carrier or excipient, such as buffered saline; a polyol (e.g., glycerol, propylene glycol, liquid polyethylene glycol and the like); carbohydrates such as glucose, mannose, sucrose or dextrans, mannitol; amino acids such as glycine; antioxidants; chelating agents such as EDTA or glutathione; preservatives or suitable mixtures thereof. In addition, a pharmaceutically acceptable carrier can include any solvent, dispersion medium, and the like which may be appropriate for a desired route of administration of the composition. The use of sustained-release delivery systems such as those disclosed by Silvestry, et al. ((1998) *Eur. Heart J.* 19 Suppl. I:I8-14) and Langtry, et al. ((1997) *Drugs* 53(5):867-84), for example, are also contemplated. The use of such carriers for pharmaceutically active substances is known in the art. Suitable carriers and their formulation are described, for example, in Remington: The Science and Practice of Pharmacy, Alfonso R. Gennaro, editor, 20th ed. Lippincott Williams & Wilkins: Philadelphia, Pa., 2000.

Agents that increase the levels of a PR peptide in the heart (i.e., purified PR39 or PR11 peptide formulations, in vivo expression vector systems or ex vivo cells expressing PR11 or PR39) can be administered to a subject via various routes. For example, such administration can be carried out by inhalation or insufflation (either through the mouth or the nose), oral, buccal, parenteral, implantation (e.g., subcutaneously or intramuscularly), or directly infused into the myocardium (e.g., via a catheter). A selected agent can be administered continuously or intermittently (e.g., every couple of days, weeks, or months) to achieve the desired effect for an extended period of time.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well-known in the art. Liquid preparations for oral administration can take the form of, for example, solutions, syrups or suspensions, or they can be presented as a dry product for constitution with water or other suitable vehicle before use. Preparations for oral administration can be suitably formulated to give controlled release of the active agent. For buccal administration the compositions can take the form of tablets or lozenges formulated in conventional manner.

For administration by inhalation, the agent for use according to the present invention is conveniently delivered in the form of an aerosol spray presentation from pressurized packs or a nebulizer, with the use of a suitable propellant, e.g., dichlorodifluoromethane, trichlorofluoromethaane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

An agent can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing or dispersing agents. Alternatively, the active agent can be in powder form for constitution with a suitable vehicle, e.g., sterile pyrogen-free water, before use.

In addition, an agent can also be formulated as a depot preparation. Such long acting formulations can be administered by implantation (for example, subcutaneously or intramuscularly) or by intramuscular injection. Thus, for example, an agent can be formulated with suitable polymeric or hydrophobic materials (for example as an emulsion in an acceptable oil) or ion exchange resins, or as sparingly soluble derivatives, for example, as a sparingly soluble salt.

An agent of the present invention can also be co-administered with another agent having similar biological activity. For example, the agent can be combined or otherwise co-administered with other therapeutics used in the treatment of heart failure, including diuretics, vasodilators and inotropic agents such as ACE inhibitors.

Toxicity and therapeutic efficacy of a selected agent can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). For any agent used in the methods of the invention, the therapeutically effective dose can be estimated initially from animal models to achieve a concentration range that includes the $IC_{50}$ (i.e., the concentration of the test agent, which achieves a half-maximal inhibition of signs or symptoms of heart failure). Such information can be used to accurately determine useful doses in humans. For example, a typical daily dose of a PR peptide may range from about 1 µg/kg to about 100 mg/kg of patient body weight or more per day, depending on the factors mentioned above.

It is contemplated, based upon the findings disclosed herein, that other pro-angiogenic agents (e.g., vascular endothelial growth factor, fibroblast growth factor, IL-8, angiogenin, angiotropin, platelet derived endothelial cell growth factor, transforming growth factor α (TGF-α) or transforming growth factor β (TGF-β)), may also be useful for increasing cardiac mass or performance.

The invention is described in greater detail by the following non-limiting examples.

Example 1

Generation of Transgenic Mice

Full-length porcine PR39 cDNA was inserted into a tetracycline-responsive vector system and a tetracycline transactivator was placed under transcriptional control of an α-myosin heavy chain promoter. The resulting tetracycline-responsive system was microinjected into fertilized mouse eggs. PCR analysis of genomic DNA from mouse tail tissue confirmed integration into the mouse genome. Independent transgenic lines were established and used for the analysis disclosed herein.

What is claimed is:

1. A method for increasing cardiac mass or performance in a subject comprising administering an effective amount of a purified proline/arginine-rich peptide comprising the amino acid sequence of SEQ ID NO:4 to a subject for at least six weeks and determining an increase in cardiac mass of at least 35% and an increase in systolic and/or diastolic performance in the subject.

2. A method for treating heart failure in a subject comprising administering an effective amount of a purified proline/arginine-rich peptide comprising the amino acid sequence of SEQ ID NO:4 to a subject for at least six weeks and determining an increase in cardiac mass of at least 35% and an increase in systolic and/or diastolic performance in the subject, thereby treating heart failure in the subject.

* * * * *

SEQUENCE LISTING

<160> NUMBER OF SEQ ID NOS: 5

<210> SEQ ID NO 1
<211> LENGTH: 172
<212> TYPE: PRT
<213> ORGANISM: Sus scrofa

<400> SEQUENCE: 1

Met Glu Thr Gln Arg Ala Ser Leu Cys Leu Gly Arg Trp Ser Leu Trp
1               5                   10                  15

Leu Leu Leu Leu Gly Leu Val Val Pro Ser Ala Ser Ala Gln Ala Leu
                20                  25                  30

Ser Tyr Arg Glu Ala Val Leu Arg Ala Val Asp Arg Leu Asn Glu Gln
            35                  40                  45

Ser Ser Glu Ala Asn Leu Tyr Arg Leu Leu Glu Leu Asp Gln Pro Pro
        50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys
                85                  90                  95

Asp Phe Lys Glu Asn Gly Arg Val Lys Gln Cys Val Gly Thr Val Thr
            100                 105                 110

Leu Asn Pro Ser Ile His Ser Leu Asp Ile Ser Cys Asn Glu Ile Gln
        115                 120                 125

Ser Val Arg Arg Arg Pro Arg Pro Pro Tyr Leu Pro Arg Pro Arg Pro
    130                 135                 140

Pro Pro Phe Phe Pro Pro Arg Leu Pro Pro Arg Ile Pro Pro Gly Phe
145                 150                 155                 160

Pro Pro Arg Phe Pro Pro Arg Phe Pro Gly Lys Arg
                165                 170

<210> SEQ ID NO 2
<211> LENGTH: 143
<212> TYPE: PRT
<213> ORGANISM: Sus scrofa

<400> SEQUENCE: 2

Gln Ala Leu Ser Tyr Arg Glu Ala Val Leu Arg Ala Val Asp Arg Leu
1               5                   10                  15

Asn Glu Gln Ser Ser Glu Ala Asn Leu Tyr Arg Leu Leu Glu Leu Asp
                20                  25                  30

Gln Pro Pro Lys Ala Asp Glu Asp Pro Gly Thr Pro Lys Pro Val Ser
            35                  40                  45

Phe Thr Val Lys Glu Thr Val Cys Pro Arg Pro Thr Arg Gln Pro Pro
        50                  55                  60

Glu Leu Cys Asp Phe Lys Glu Asn Gly Arg Val Lys Gln Cys Val Gly
65                  70                  75                  80

Thr Val Thr Leu Asn Pro Ser Ile His Ser Leu Asp Ile Ser Cys Asn
                85                  90                  95

Glu Ile Gln Ser Val Arg Arg Arg Pro Arg Pro Pro Tyr Leu Pro Arg
            100                 105                 110

Pro Arg Pro Pro Pro Phe Phe Pro Pro Arg Leu Pro Pro Arg Ile Pro
        115                 120                 125

Pro Gly Phe Pro Pro Arg Phe Pro Pro Arg Phe Pro Gly Lys Arg
    130                 135                 140

```
<210> SEQ ID NO 3
<211> LENGTH: 39
<212> TYPE: PRT
<213> ORGANISM: Sus scrofa

<400> SEQUENCE: 3

Arg Arg Arg Pro Arg Pro Pro Tyr Leu Pro Arg Pro Arg Pro Pro Pro
1               5                   10                  15
Phe Phe Pro Pro Arg Leu Pro Pro Arg Ile Pro Pro Gly Phe Pro Pro
            20                  25                  30
Arg Phe Pro Pro Arg Phe Pro
        35

<210> SEQ ID NO 4
<211> LENGTH: 11
<212> TYPE: PRT
<213> ORGANISM: Sus scrofa

<400> SEQUENCE: 4

Arg Arg Arg Pro Arg Pro Pro Tyr Leu Pro Arg
1               5                   10

<210> SEQ ID NO 5
<211> LENGTH: 658
<212> TYPE: DNA
<213> ORGANISM: Sus scrofa

<400> SEQUENCE: 5
gggctcacct gggcaccatg agacccaga  gggccagcct gtgcctgggg cgctggtcac    60
tgtggcttct gctgctggca ctcgtggtgc cctcggccag cgcccaggcc ctcagctaca   120
gggaggccgt gcttcgtgct gtggatcgcc tcaacgagca gtcctcggaa gctaatctct   180
accgcctcct ggagctggac cagccgccca aggccgacga ggacccgggc accccgaaac   240
ctgtgagctt cacggtgaag gagactgtgt gtcccaggcc gacccggcag ccccggagc    300
tgtgtgactt caaggagaat gggcgagtga agcagtgtgt ggggacagtc accttgaacc   360
catccattca ctcactggac atctcctgta atgagattca gagtgtcagg agacgtcccc   420
gacccccata tttgccaagg ccaaggccac ctccgttttt cccaccaagg ctcccaccaa   480
ggatcccacc agggttccca ccaaggttcc caccacggtt ccccggaaaa cggtgatgga   540
gtggctgata acatacccat taaaagcttt tggtgaatcc tgagcccagg gaaagtccta   600
ggatcttatt gttgtggctc agacttctga accatgaaaa ataaattctt gtgaaacg     658
```